United States Patent [19]
Lin

[11] Patent Number: 5,613,968
[45] Date of Patent: Mar. 25, 1997

[54] UNIVERSAL PAD FIXATION DEVICE FOR ORTHOPEDIC SURGERY

[76] Inventor: Chih-I Lin, 14292 Spring Vista La., Chino Hills, Calif. 91709

[21] Appl. No.: 431,739

[22] Filed: May 1, 1995

[51] Int. Cl.⁶ ........................................ A61B 17/56
[52] U.S. Cl. .............................. 606/61; 606/73; 411/389; 411/537
[58] Field of Search ................... 606/61, 60, 72, 606/73, 54, 53; 411/537, 389, 396, 400

[56] References Cited

PUBLICATIONS

Hiromi Maysuzaki et al., "Problems and Solutions of Pedicle Screw Plate Fixation of Lumbar Spine", Spine, vol. 15, No. 11 (1990), pp. 1159 – 1164.

*Primary Examiner*—Michael Powell Buiz
*Assistant Examiner*—David O. Reip
*Attorney, Agent, or Firm*—Bacon & Thomas

[57] ABSTRACT

An orthopedic fixation device includes a fixation ring, a universal pad, a threaded fixation element, and a fastening nut. The universal pad contains a circular hole and is provided at one end with a protruding arcuate surface and at another end with a recessed arcuate surface concentric with the protruding arcuate surface. The fastening nut is provided with a protruding or recessed arcuate surface located at one side facing the universal pad. The threaded fixation element has an arresting portion which is provided with a protruding or recessed arcuate surface located at one side facing the universal pad. The protruding and recessed arcuate surfaces of the fastening nut and the threaded fixation element are engageable with the universal pad.

8 Claims, 6 Drawing Sheets

5,613,968

UNIVERSAL PAD FIXATION DEVICE FOR ORTHOPEDIC SURGERY

FIELD OF THE INVENTION

The present invention relates generally to an orthopedic device, and more particularly to a universal pad fixation device for treating a fractured bone.

BACKGROUND OF THE INVENTION

The threaded fixation element, such as a threaded rod or bone nail, and the fluted fixation element, such as a fixation plate or lateral fixation block, of the conventional bone fixing device are generally defective in design in that they do not meet to form exactly an angle of 90 degrees, and that the nut cannot be fastened securely with the threaded fixation element. With a view to overcoming such shortcomings as described above, the U.S. Pat. Nos. 4,611,581 and 4,696,290 disclosed respectively a bone fixing plate which is provided with scallops intended to enhance the effect of fastening the threaded fixation element with the fluted fixation element of the conventional bone fixing device. However, the bone fixing plates disclosed in the above-mentioned U.S. patents fail to provide an effective remedial measure. As a result, an improved system was disclosed by Hiromi Matsuzaki, et al. in SPINE, VOLUME 15, NUMBER 11 (1990), pp. 1159–1164. The improved system comprises a fluted fixation element which is provided respectively on both faces of the slot or the through hole thereof with a recessed arcuate surface capable of cooperating with a protruding arcuate surface of an arresting portion of the fixation element having the threaded portion and the arcuate protruding surface of the fixation nut. In view of the fact that the centers of the circles of these two arcuate recessed surfaces are fixed, the fixation element is located on a line connecting these two centers of circles when the fixation nut is tightened. In other words, when the fixation nut is tightened, the fixation element having the threaded portion and the fixation element having the slot form an angle which is fixed and cannot be changed. However, the angle can be adjusted slightly if the fixation nut is not tightened. It must be noted here that the fixation nut must be tightened so as to enable the fixation device to work effectively. Furthermore, the disclosure of the U.S. Pat. No. 4,854,311 comprises a washer which has a specific angle and is located between the threaded fixation element and the fluted fixation element. However, an addition of the washer can often complicates the surgical process.

SUMMARY OF THE INVENTION

It is therefore the primary objective of the present invention to provide a universal pad fixation device for an orthopedic surgery, which can be adjusted angularly.

It is another objective of the present invention to provide a universal pad fixation device for an orthopedic surgery, which comprises arcuate protruding surfaces/arcuate recessed surfaces as connection means.

It is still another objective of the present invention to provide a universal pad fixation device for an orthopedic surgery, which comprises a fixation ring, a universal pad, a threaded fixation element, and a fastening nut.

The fixation ring is provided with a slot or through hole.

The universal pad is provided at one end thereof with a protruding arresting edge and at another end thereof with a plurality of slits. The universal pad is further provided centrally with a circular body engageable with the through hole of the fixation ring.

The threaded fixation element is provided on a threaded portion thereof with an arresting portion which is so dimensioned such that the slit end of the universal pad is stopped by the arresting portion when said threaded portion of said threaded fixation element is received in a circular hole of the circular body of the universal pad.

The fastening nut is engaged with the threaded fixation element such that the nut is stopped by the protruding arresting edge of the universal pad.

The present invention is characterized in that the universal pad is provided at one end of the circular body thereof with a protruding arcuate surface and at another end thereof with a recessed arcuate surface, which are substantially concentric. The fastening nut is provided with a recessed arcuate surface located on one surface thereof facing the universal pad while the threaded fixation element is provided with a protruding arcuate surface located on the arresting portion thereof facing the universal pad. These arcuate protruding surface and arcuate recessed surface are capable of cooperating with the arcuate recessed surface and the arcuate protruding surface of the universal pad respectively.

The fixation ring of the present invention can be fastened to a fixation rod by means of the fastening nut of the present invention or to two fixation rods.

If desired, the slit end of the universal pad may be provided with a protruding arresting edge. It is preferable that the slit end of the universal pad is provided with an arcuate recessed surface, and that another end opposite to the slit end is provided with the arcuate protruding surface, and further that the arcuate recessed surface and the arcuate protruding surface are concentric.

The universal pad of the present invention is provided with a hole, which may be cylindrical or conical in construction, preferably conical in construction.

The threaded fixation element of the present invention may be similar in construction to any threaded fixation element of the prior art, such as the threaded fixation rod or the double-threaded bone screw. The threaded fixation rod is used in conjunction with other component parts while the double-threaded bone screw is used in such a manner that the nailing portion of the double-threaded bone screw is fastened onto a bone or vertebra.

The threaded fixation element of the present invention is provided on a threaded portion thereof with an arresting portion which is made integrally with the threaded fixation element. The arresting portion may comprise of a radially protruding edge of said threaded fixation element and an arcuate washer. In addition, the arresting portion may be replaced by a fastening nut. In other words, both sides of the universal pad are urged respectively by a fastening nut.

If the universal pad of the present invention is provided at one end thereof with the arcuate protruding surface, the arresting portion of the threaded fixation element of the present invention should be provided with an arcuate recessed surface located on a surface thereof facing the one end of the universal pad. On the other hand, if the universal pad of the present invention is provided at one end thereof with the arcuate recessed surface, the arresting portion of the threaded fixation element of the present invention should be provided with the arcuate protruding surface located on one surface thereof facing the one end of the universal pad.

The fastening nut of the present invention is provided on one surface thereof with an arcuate recessed surface facing the arcuate protruding surface located at one end of the universal pad of the present invention. On the other hand, the fastening nut of the present invention may be provided on one surface thereof with an arcuate protruding surface facing the arcuate recessed surface located at one end of the universal pad.

The circular body of the universal pad of the present invention has an outer diameter substantially equal to or slightly smaller than the smallest width of the opening of the fixation ring the present invention, so as to ensure that the universal pad and the fixation ring are joined together firmly. The hole of the universal pad has an inner diameter greater than the outer diameter of the threaded portion of the threaded fixation element of the present invention. As a result, the threaded fixation element can be disposed in the hole of the universal pad such that the longitudinal axis of the threaded fixation element and the longitudinal axis of the hole of the universal pad form an acute angle.

Assuming that the present invention comprises a fixation bone plate having a round through hole, a universal pad which is provided at one end thereof with a protruding arcuate surface having a radius r2 and is provided at another end thereof with a recessed arcuate surface having a radius r1 and being concentric with the protruding arcuate surface, a double-threaded bone screw, and a fastening nut, the fastening process of the present invention comprises the steps of: (i) fastening the nail portion of the bone screw onto a vertebra; (ii) inserting the universal pad into the round through hole of the fixation bone plate such that the universal pad is stopped by the arresting protruding edge; (iii) fitting the hole of the universal pad over the threaded portion of the double-threaded bone screw such that the universal pad is stopped by the arresting portion; and (iv) fastening the nut in such a manner that the universal pad is urged by the nut and that the another end of the universal pad joins intimately with the edge of the slot or through hole of the fixation plate. In view of the fact that the fastening method of the present invention is attained by means of the protruding arcuate surface and the recessed arcuate surface, which can be caused to join with each other without forming therebetween a gap when the universal pad is urged intensively by the nut, even when the double-threaded bone screw and the fixation plate are not perpendicular to each other. Furthermore, the one end and the another end of the universal pad are concentric so as to enable the universal pad to be urged by the fastening nut to such an extent that there is a smallest distance (r2–r1) between the fastening nut and the arresting portion of the double-threaded bone screw.

The foregoing objectives, features and functions of the present 15 invention will be more readily understood upon a thoughtful deliberation of the following detailed description of the embodiments of the present invention in conjunction with the accompanying drawings.

DETAILED DESCRIPTION OF THE EMBODIMENTS

Figure 1A:
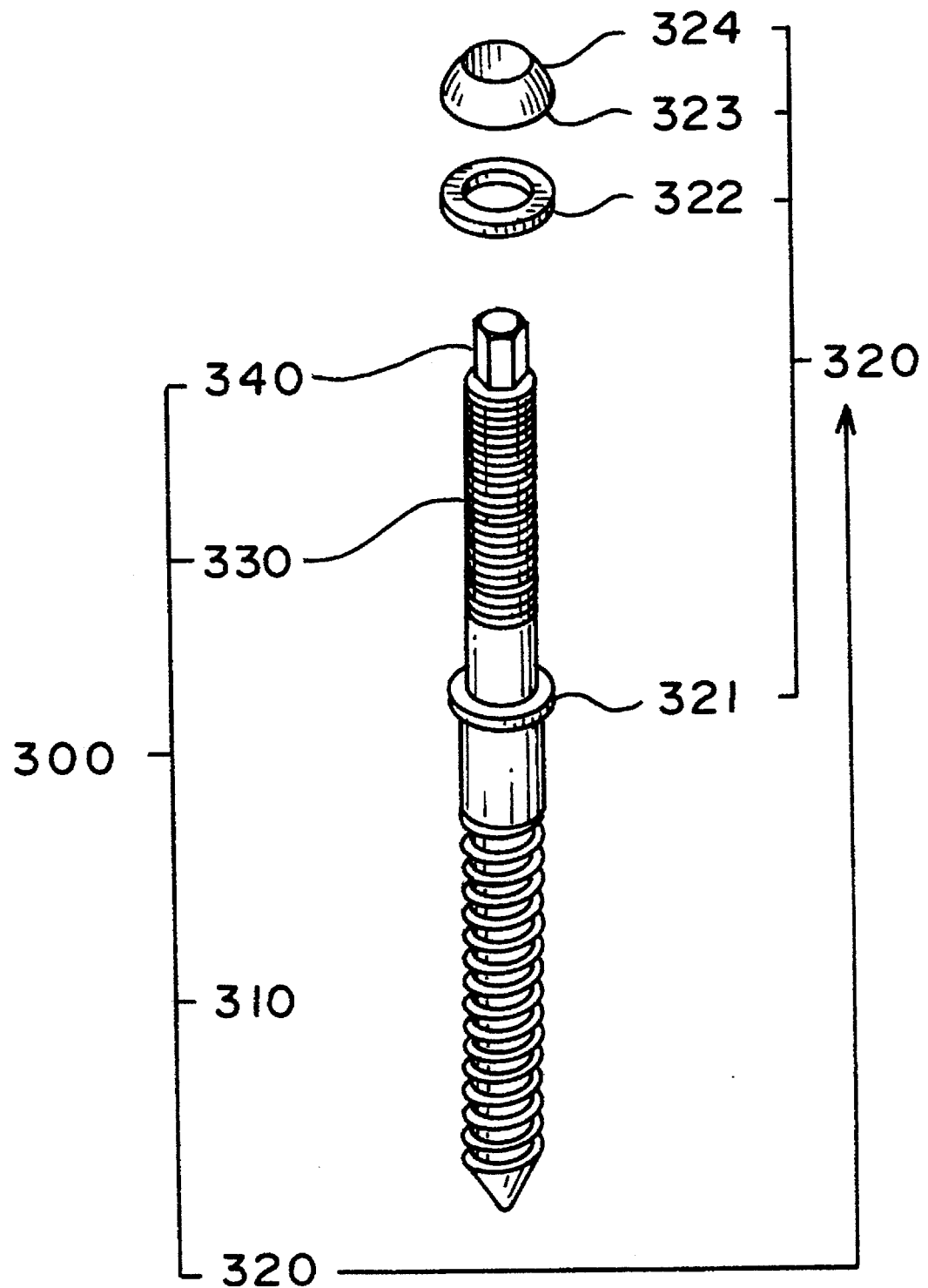
FIGS. 1a and 1b are schematic views of a first preferred embodiment of the present invention.
Figure 1B:
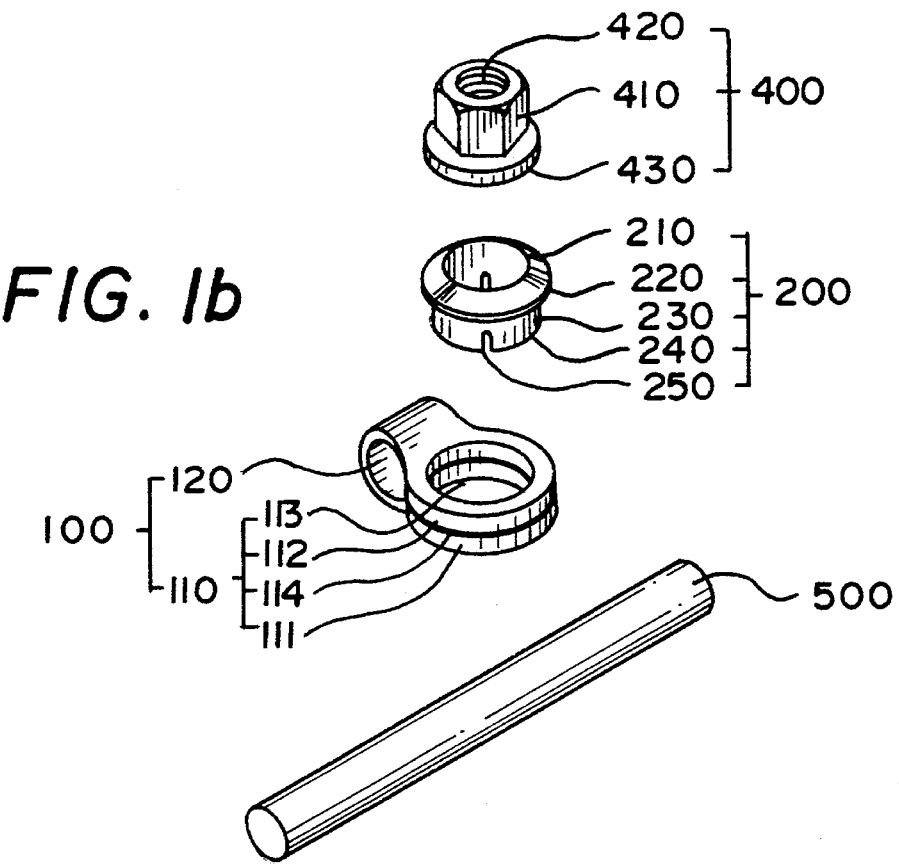

As shown in FIG. 1a, the present invention comprises a double-threaded screw 300 (a threaded fixation element) which is provided with a first threaded portion 310 for fastening onto a vertebra, an arresting portion 320 and a second threaded portion 330 having a tool guiding head 340. The arresting portion 320 is composed of a protruding edge 321, a height adjusting washer 322, and an arcuate washer 323 having a protruding arcuate surface 324. As shown in FIG. 1b, the present invention further comprises a fixation ring 100, a universal pad 200, a fastening nut 400, and a fixation rod 500. The fixation ring 100 has a fitting portion 110 and a fixing portion 120. The fitting portion 110 is fitted over the second threaded portion 330 of FIG. 1a while the fixing portion 120 is fitted over the fixation rod 500. The fitting portion 110 has a lower fitting ring 111, an upper fitting ring 112, a ring hole 113 and a slit 114 located between the lower fitting ring 111 and the upper fitting ring 112. The universal pad 200 has a protruding arcuate surface 210, a protruding arresting edge 220, a circular body 230, a plurality of slits 250 and a recessed arcuate surface 240 capable of cooperating with the protruding arcuate surface 324 of the arcuate washer 323 of FIG. 1a.

Figure 2:
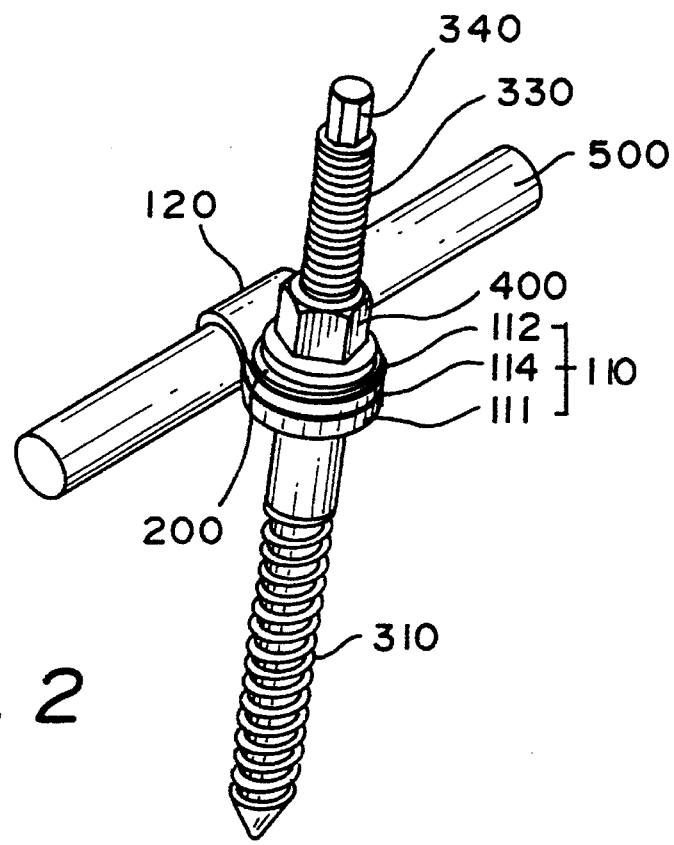
FIG. 2 shows another schematic view of the first preferred embodiment of the present invention.

The reference numerals of FIG. 2 are similar in definition to the like reference numerals of FIGS. 1a and 1b. As shown in FIGS. 1a, 1b and 2, the fixing portion 120 of the fixation ring 100 is fitted over the fixation rod 500 while the fitting portion 110 is fitted over the second threaded portion 330 of the double-threaded screw shown in FIG. 1a. Thereafter, the universal pad 200 is fitted over the second threaded portion 330 of the double-threaded screw such that the circular body 230 of the universal pad 200 is located between the second threaded portion 330 and the ring hole 113, and that the recessed arcuate surface 240 is engaged with the protruding arcuate surface 324 of the arcuate washer 323. The fastening nut 400 is fastened with the second threaded portion 330 so as to cause the lower fitting ring 111 and the upper fitting ring 112 to hold together intimately. In the meantime, the fixation ring 100 is fastened firmly with the fixation rod 500. The recessed arcuate surface 430 of the nut 400 is engaged with the protruding arcuate surface 210.

Figure 3A:
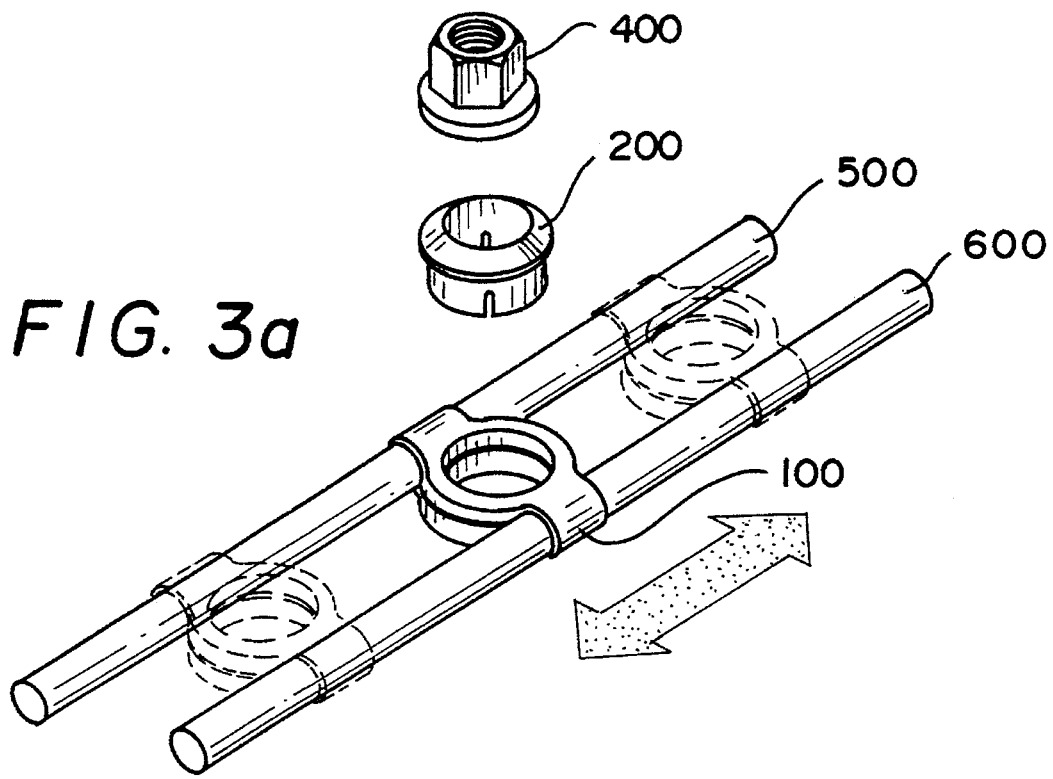
FIGS. 3a, 3b, 3c are schematic and sectional views of a second preferred embodiment of the present invention.
Figure 3B:
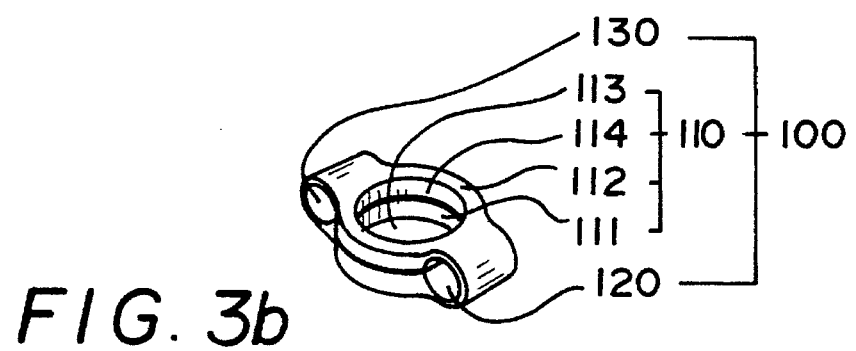
Figure 3C:
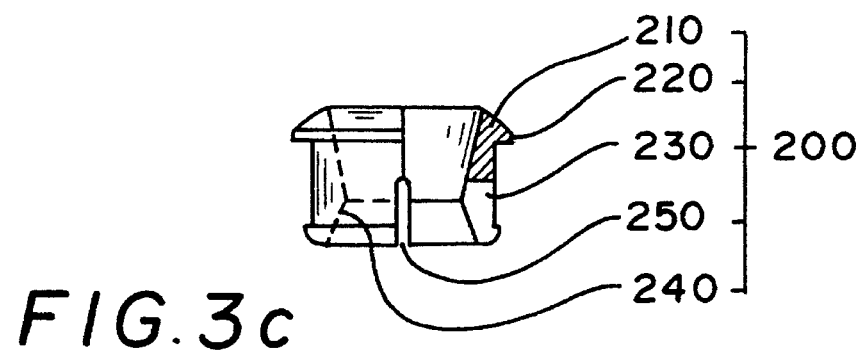

As shown in FIG. 3a, the present invention comprises two fixation rods 500 and 600. The reference numerals of 100, 110, 111, 112, 113 and 114 of FIG. 3b are the same in definition to the like reference numerals of FIG. 1b. The reference numerals of 200, 210, 220, 230, 240 and 250 of FIG. 3c are the same in definition to the like reference numerals of FIG. 1b. The fixation ring 100 may have two fixing portions 120. As illustrated by arrow in FIG. 3a, the fixation ring 100 and the fixation rods 500, 600 are fastened adjustably.

Figure 4:
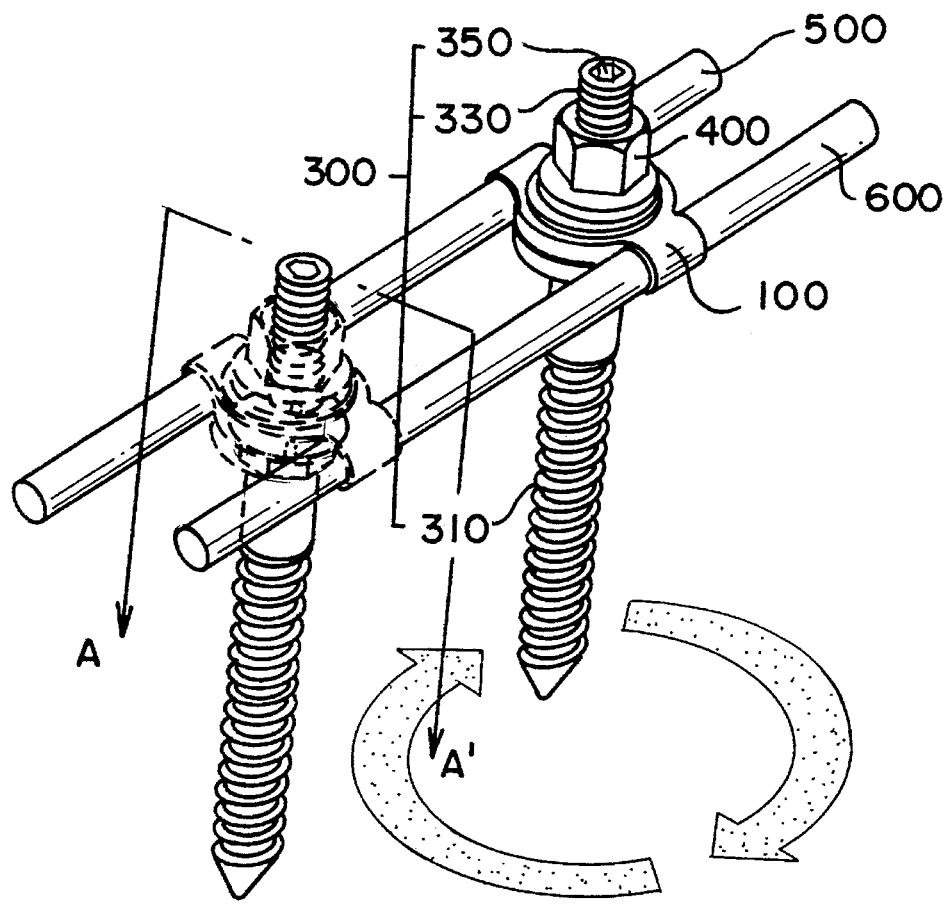
FIG. 4 shows another schematic view of the second preferred embodiment of the present invention.
Figure 5:
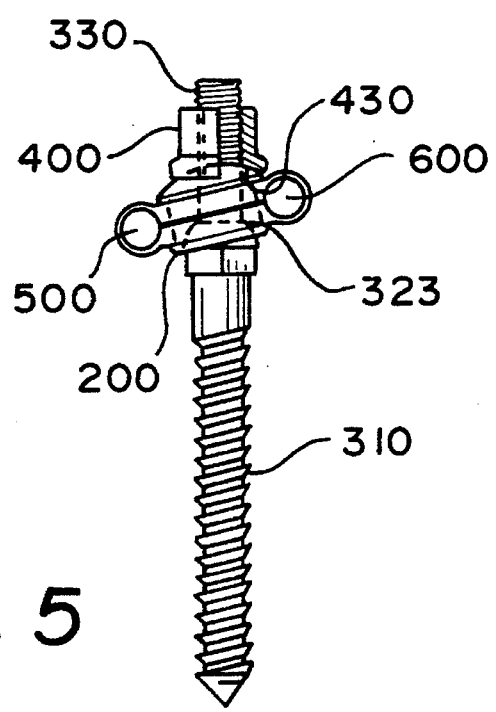
FIG. 5 shows a sectional view of a portion taken along the direction indicated by a line AA' as shown in FIG. 4.

The reference numerals of 100, 300, 310, 330, 400, 500 and 600 of FIG. 4 are similar in definition to the reference numerals of FIGS. 1a, 1b, 3a, 3b and 3c. The tool hole 350 replaces the tool guiding head 340 of FIG. 1a. The fastening method is similar to that shown in FIG. 2. The universal pad 200 is located between the fixation ring 100 and the second threaded portion 330. As a result, the fixation ring 100 and the fixation rods 500, 600, and the double-threaded screw 300 form an angle, which can be adjusted slightly, as shown in FIG. 5.

Figure 6:
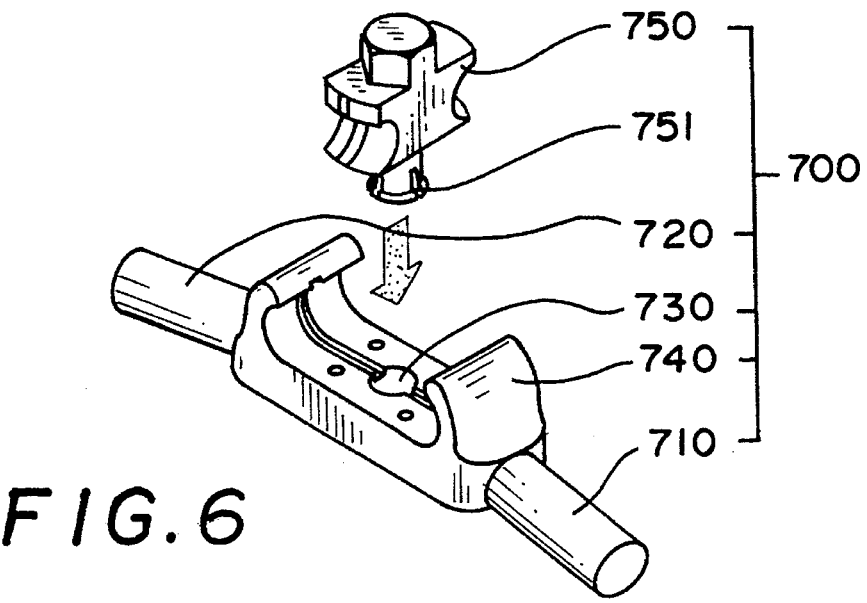
FIG. 6 shows a schematic view of a fixation device which has centrally two fixation rods and is employed in conjunction with the present invention.

The present pad fixation device may be used with the fixation device disclosed in U.S. patent application Ser. No. 08/431,741, as shown in FIG. 6. The fixation device comprises a fixation main body 700 having a right fixation rod 710, a left fixation rod 720, a retaining hole 730 and two fixation pieces 740; and a rotatable clamping block 750 having a clamping projection 751 engageable with the retaining hole 730.

Figure 7:
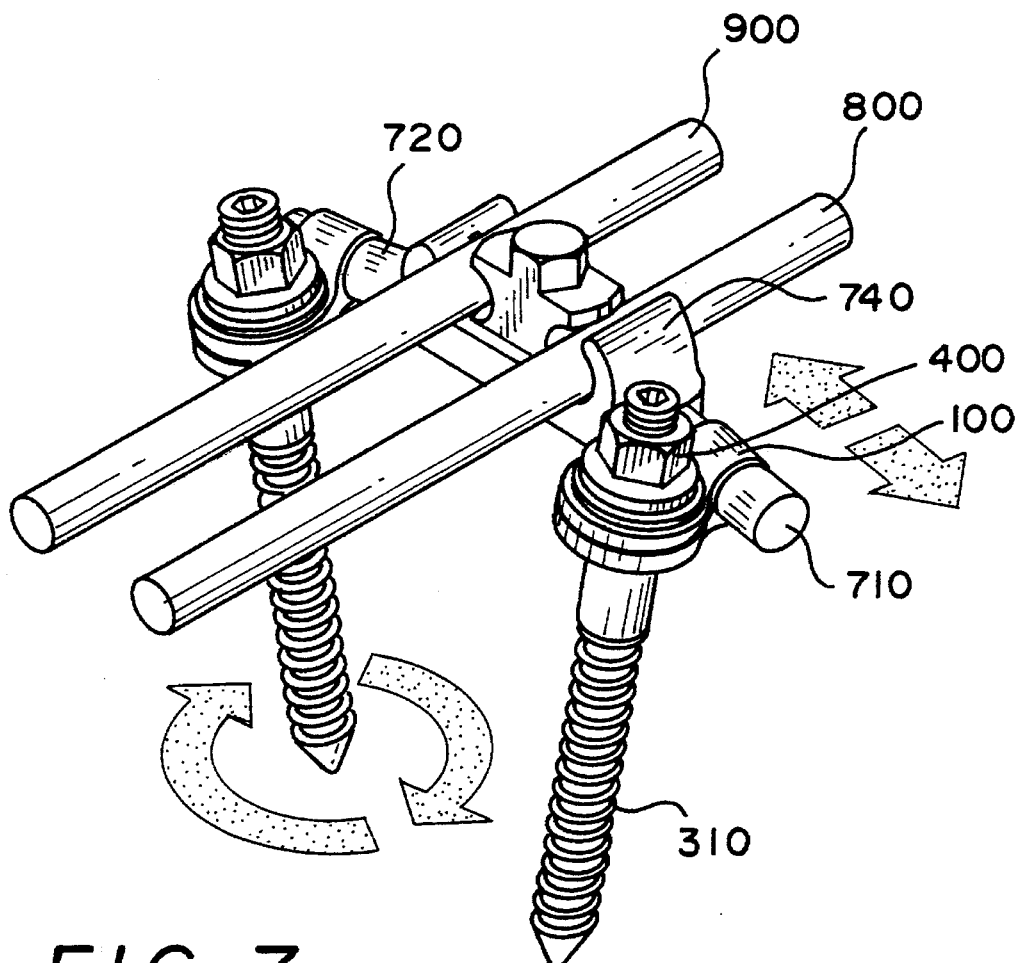
FIG. 7 is a perspective view showing the combination of the fixation device of FIG. 6 with the present invention.

The reference numerals of 100, 310 and 400 of FIG. 7 are the same in definition to the like reference numerals of FIGS. 1a, 1b and 6. As shown in FIG. 7, the present invention comprises two fixation rods 800 and 900.

Figure 8:
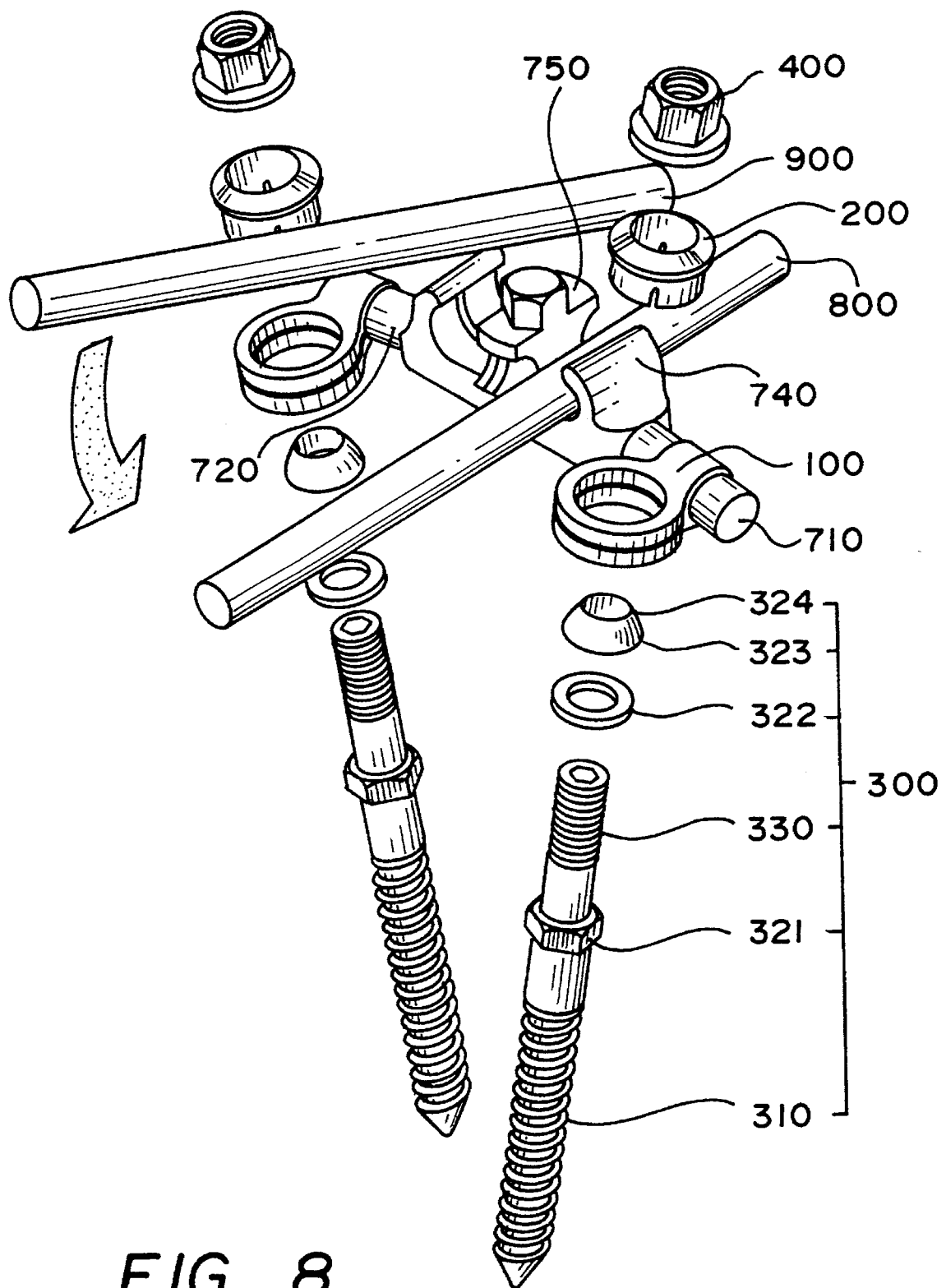
FIG. 8 is an exploded view of the embodiment as shown in FIG. 7.

The reference numerals of FIG. 8 are similar in definition to the like reference numerals of FIGS. 1a, 1b and 7. As shown in FIGS. 7 and 8, the double-threaded screw 300, the fixation ring 100, the universal pad 200 and the fastening nut 400 may be fastened firmly with the right fixation rod 710 and the left fixation rod 720 in a manner similar to that shown in FIGS. 1a, 1b and 2.

What is claimed is:

1. A universal pad fixation device for orthopedic surgery comprising:

a fixation ring having a through hole;

a universal pad located on the fixation ring and provided with a first arresting surface and at an end thereof with a plurality of slits, said universal pad further having a circular body with a circular hole therethrough, said circular body engageable with said through hole of said fixation ring a threaded fixation element provided with a threaded portion and an arresting portion, said threaded portion extending through said circular hole of said universal pad so as to cause the slit end of said universal pad to stop at said arresting portion; and a fastening nut engageable with said threaded portion of said threaded fixation element the fastening nut having a second arresting surface such that said fastening nut is arrested by contact of said second arresting surface with said first arresting surface of said universal pad;

wherein one of said first and second arresting surfaces is a protruding arcuate surface and the other of said first and second arresting surfaces is recessed arcuate surface;

said end of said universal pad has a recessed arcuate surface concentric with said first arresting surface; and said arresting portion of said threaded fixation element has a recessed arcuate surface located on a side thereof facing said universal pad when said fastening nut has a protruding arcuate arresting surface, and a protruding arcuate surface located on one side thereof facing said universal pad when said fastening nut has a recessed arcuate arresting surface;

wherein said arcuate surface of said fastening nut and said arcuate surface of said arresting portion of said threaded fixation element are respectively engageable with said arcuate surface of said universal pad.

2. The universal pad fixation device as defined in claim 1, wherein said threaded fixation element comprises a double-threaded screw.

3. The universal pad fixation device as defined in claim 1, wherein said threaded fixation element comprises a threaded rod.

4. The universal pad fixation device as defined in claim 1, wherein said arresting portion of said threaded fixation element is integrally formed on said threaded fixation element.

5. The universal pad fixation device as defined in claim 1, wherein said arresting portion of said threaded fixation element comprises a radially protruding edge on said threaded fixation element and a height adjusting washer having a protruding arcuate surface.

6. The universal pad fixation device as defined in claim 1, wherein said fixation ring comprises means to engage a fixation member of another fixation device for orthopedic surgery.

7. The universal pad fixation device as defined in claim 4, wherein said fixation ring comprises means to engage a fixation member of another fixation device for orthopedic surgery.

8. The universal pad fixation device as defined in claim 5, wherein said fixation ring comprises means to engage a fixation member of another fixation device for orthopedic surgery.

\* \* \* \* \*